US007500779B2

(12) United States Patent
Takeuchi et al.

(10) Patent No.: US 7,500,779 B2
(45) Date of Patent: Mar. 10, 2009

(54) THERMAL ANALYSIS APPARATUS

(75) Inventors: Toshitada Takeuchi, Chiba (JP);
Masakatsu Hasuda, Chiba (JP)

(73) Assignee: SII NanoTechnology Inc. (JP)

( * ) Notice: Subject to any disclaimer, the term of this patent is extended or adjusted under 35 U.S.C. 154(b) by 65 days.

(21) Appl. No.: 11/705,669

(22) Filed: Feb. 13, 2007

(65) Prior Publication Data

US 2007/0201533 A1    Aug. 30, 2007

(30) Foreign Application Priority Data

Feb. 28, 2006    (JP)    ............................. 2006-052602

(51) Int. Cl.
*G01N 25/00* (2006.01)
(52) U.S. Cl. .............................. 374/14; 374/10; 374/31
(58) Field of Classification Search .................. 374/14, 374/10, 31
See application file for complete search history.

(56) References Cited

U.S. PATENT DOCUMENTS

| | | | | |
|---|---|---|---|---|
| 4,606,649 A | * | 8/1986 | Mikhail | ........................ 374/10 |
| 4,763,536 A | * | 8/1988 | Beshoory | ................... 73/865.6 |
| 5,306,087 A | * | 4/1994 | Nakamura et al. | ............ 374/14 |
| 5,321,719 A | * | 6/1994 | Reed et al. | ..................... 374/14 |
| 5,466,066 A | * | 11/1995 | Hidaka | ......................... 374/14 |
| 5,588,746 A | * | 12/1996 | Minobe et al. | ................. 374/10 |

FOREIGN PATENT DOCUMENTS

| JP | 04361145 A | * | 12/1992 |
|---|---|---|---|
| JP | 11326249 | | 11/1999 |

* cited by examiner

*Primary Examiner*—Gail Verbitsky
*Assistant Examiner*—Mirellys Jagan
(74) *Attorney, Agent, or Firm*—Adams & Wilks

(57) ABSTRACT

A thermal analysis apparatus possesses has a cylindrical furnace tube axially inserted in a cylindrical heating furnace, and a pair of sample holders extending axially inside the furnace tube. The furnace tube is supported by two axially spaced groups of butting members, each group having three or more butting members that are disposed in circumferentially spaced-apart relationship on the outside of the furnace tube and that butt against the furnace tube to restrain positional deviation thereof in a radial direction while permitting expansion and contraction thereof in the axial direction during heating of the furnace tube by the heating furnace.

20 Claims, 4 Drawing Sheets

THERMAL ANALYSIS APPARATUS

BACKGROUND OF THE INVENTION

The present invention relates to a thermal analysis apparatus in which a sample is heated and a physical change of the sample following upon a temperature change is measured.

From olden times, as a method of evaluating a temperature characteristic of the sample, there is performed a method called a thermal analysis in which the sample is heated and the physical change of the sample following upon the temperature change is measured. As the thermal analysis like this, from its object, although various methods are proposed, there are, e.g., a differential thermal analysis in which the sample and a reference material are heated while being juxtaposed and a relative change in a temperature is measured, a thermogravimetric analysis in which a weight change of the sample following upon the temperature change is measured, and the like.

For example, as an apparatus for performing the thermogravimetric analysis, there is proposed a thermal analysis apparatus having possessed a furnace tube which is like a cylinder and in whose inside there is formed a sample chamber, a heating furnace which is surrounded by a side face of the furnace tube and heats the sample chamber through the furnace tube, a sample holding part which holds the sample, a thermocouple which is provided in the sample holding part and detects a temperature of the sample, and a weight detector which is provided in the sample holding part and can measure the weight change of the sample (e.g., refer to Patent Document 1). In the thermal analysis apparatus like this, by inserting the sample having been held by the sample holding part into an inside of the furnace tube, heating it by the heating furnace, measuring the temperature of the sample by the thermocouple, and measuring a weight of the sample by the weight detector, it is deemed that the weight change of the sample following upon the temperature change can be measured.

Further, in recent years, there are also proposed a thermal analysis apparatus in which the thermogravimetric analysis is performed like the above by additionally providing, together with the sample holding part like this, which holds the sample, a separate sample holding part which holds the reference material, and a separate thermocouple which measures a temperature of the reference material, and in which the differential thermal analysis can be performed as well by measuring a relative change in temperatures of the sample and the reference material, and the like.

[Patent Document 1] JP-A-11-326249 Gazette

However, in such a thermal analysis apparatus as shown in the Patent Document 1, when heating the sample by being inserted into the inside of the furnace tube, also the furnace tube expands or contracts following upon the temperature change. Therefore, the sample having been disposed in the inside of the furnace tube changes in its relative position in an axial direction and a radial direction of the furnace tube following upon the temperature change of the furnace tube. While an inside of the furnace tube having been heated by the heating furnace is uniform in its temperature distribution in the axial direction, in the radial direction it has a steep temperature distribution toward a center. Therefore, in a case where the furnace tube has position-deviated in the radial direction, there has been a problem that a heating environment of the sample changes, so that a precise measurement becomes impossible to be performed.

This invention is one having been made in view of the circumstances having been mentioned above, and one providing a thermal analysis apparatus in which there is no fact that, when heating the sample, the furnace tube position-deviates due to the temperature change, and the thermal analysis can be performed by heating the sample always in a constant heating environment.

SUMMARY OF THE INVENTION

In order to solve the above problems, this invention provides the following means.

A thermal analysis apparatus of the present invention is characterized by possessing a support base, a heating furnace which is approximately like a cylinder, and whose inside can be raised in its temperature till a predetermined heating temperature, a heating furnace fixation part fixing the heating furnace to the support base, a furnace tube which is approximately like the cylinder, inserted through the heating furnace while having an interstice, and has been fixed in its base end part to the support base by a fixation member, a fixation means which makes the furnace tube capable of expanding or contracting in an axial direction, and positioning-fixes it in a radial direction, a sample holding means which holds a sample in an inside of a heating part of the furnace tube, that is a range capable of being heated by the heating furnace, and a temperature measurement means measuring a temperature change of the sample.

According to the thermal analysis apparatus concerned with this invention, by the fact that while the heating furnace is fixed to the support base by the heating furnace fixation part, also the furnace tube is fixed in its base end part to the support base by the fixation member, the furnace tube keeps a state in which it has been inserted through the heating furnace while having the interstice. And, the heating furnace is raised in its temperature with the sample being disposed by the sample holding means in the inside of the heating part of the furnace tube. The sample is heated in the inside of the furnace tube and, following upon this, by measuring a temperature of the sample by the temperature measurement means, it is possible to evaluate a temperature characteristic of the sample. On this occasion, by raising the heating furnace in its temperature, the furnace tube is also heated, and the furnace tube generates an expansion or a contraction in an axial direction and a radial direction. By the fact that the furnace tube is fixed in its base end part by the fixation member and can expand or contract in the axial direction by the fixation means, even if the temperature has changed, it is possible to freely expand or contract in the axial direction without the fact that a stress occurs. On the other hand, by the fact that, in the radial direction, it is positioned and fixed by the fixation means, a positional deviation in the radial direction following upon the temperature change is prevented, and a position of the sample in the radial direction in the inside of the furnace tube is made constant, so that a heating environment of the sample can be kept always constant.

Further, it is deemed to be more desirable that, in the above thermal analysis apparatus, the fixation means is provided in both-side two places in a tip side and a base end side of the heating part of the furnace tube.

According to the thermal analysis apparatus concerned with this invention, by the fact that it is positioning-fixed in the radial direction by the fixation means in both sides of the heating part of the furnace tube in which the expansion or the contraction occurs due to the temperature change, the positional deviation to the radial direction following upon the temperature change can be more certainly prevented.

Further, it is deemed to be more desirable that, in the above thermal analysis apparatus, the fixation means is provided in the heating furnace fixation part, and the furnace tube is fixed to the support base by the fixation means through the heating furnace fixation part.

According to the thermal analysis apparatus concerned with this invention, both the furnace tube to be heated and the heating furnace which heats the furnace tube are fixed to the support base through the heating furnace fixation part, i.e., fixed by the same fixation system. Therefore, a relative positional relation between the heating furnace and the furnace tube can be kept constant, so that the heating environment of the sample can be additionally stabilized.

Further, it is deemed to be more desirable that, in the above thermal analysis apparatus, the fixation means is constituted by at least three butting members which butt against the furnace tube, and the furnace tube is butting-supported in at least three places in a circumferential direction by the butting members.

According to the thermal analysis apparatus concerned with this invention, by the fact that the furnace tube is butting-supported in at least three places in the circumferential direction by the butting members, while the furnace tube slides with respect to the butting members and can expand or contract in the axial direction, in the radial direction it is certainly positioned and fixed.

Further, it is deemed to be more desirable that, in the above thermal analysis apparatus, the butting member of the fixation means is approximately like a column, fixed with respect to the support base by a fixation bolt, and a columnar piece whose peripheral face part butts against the furnace tube.

According to the thermal analysis apparatus concerned with this invention, by the fact that the butting member butting-supported to the furnace tube is the columnar piece approximately like the column, a contact with the furnace tube is made a line contact, so that there can be fixed with a contacting range being made minimum. Therefore, it is possible to suppress a heat transfer from the furnace tube to the columnar piece, the sample can be efficiently heated, and it is possible to prevent the columnar piece, which is the butting member, or the fixation bolt from being heated and expanding or contracting.

Further, it is deemed to be more desirable that, in the above thermal analysis apparatus, the columnar piece is formed by ceramics.

According to the thermal analysis apparatus concerned with this invention, by the fact that the columnar piece is formed by ceramics, it is possible to additionally suppress the heat transfer to the columnar piece, the sample can be efficiently heated, and it is possible to suppress the expansion or the contraction of the columnar piece by the fact that it is heated.

Further, it is deemed to be more desirable that, in the above thermal analysis apparatus, the columnar piece of the fixation means is fixed while being made eccentric with respect to the fixation bolt.

According to the thermal analysis apparatus concerned with this invention, since the columnar piece is made eccentric with respect to the fixation bolt, by changing a direction in which the columnar piece is fixed with the fixation bolt being made a center, it is possible to finely adjust a radial position of the furnace tube butted against and fixed to the columnar piece. By this mechanism, it is possible to adjust the sample to a center position in which a temperature gradient of the furnace tube is smallest.

Further, it is deemed to be more desirable that, in the above thermal analysis apparatus, it possesses a weight measurement means measuring a weight of the sample having been held by the sample holding means.

According to the thermal analysis apparatus concerned with this invention, there is no fact that the furnace tube position-deviates in the radial direction following upon the temperature change, and it is possible to precisely measure a weight change following upon the temperature change of the sample by heating the sample in a constant heating environment.

Further, it is deemed to be more desirable that, in the above thermal analysis apparatus, the sample holding means and the corresponding temperature measurement means are provided respectively by two so as to be capable of disposing different samples while being made approximately axisymmetric with respect to a center axis of the furnace tube.

According to the thermal analysis apparatus concerned with this invention, there is no fact that the furnace tube position-deviates in the radial direction following upon the temperature change, and it is possible to heat the constant and different samples in a relatively equal heating environment. Therefore, with one sample being made a reference, it is possible to precisely measure a relative temperature change of the other sample.

According to the thermal analysis apparatus of the present invention, by the fact that the furnace tube having been fixed in its base end part by the fixation member is positioning-fixed additionally by the fixation means, there is no fact that the furnace tube position-deviates in the radial direction due to the temperature change, and the thermal analysis can be performed by heating the sample always in the constant heating environment.

DETAILED DESCRIPTION OF THE PREFERRED EMBODIMENT

FIG. 1 to FIG. 4 show an embodiment concerned with this invention. A thermal analysis apparatus 1 of this embodiment is a differential thermal/thermogravimetric simultaneous measurement apparatus in which different samples of a measurement sample S1 and a reference sample S2 are heated in a constant heating environment, respective temperature changes are measured, and weights of the measurement sample S1 and the reference sample S2 are measured. Hereunder, details are shown about its constitution.

Figure 1:
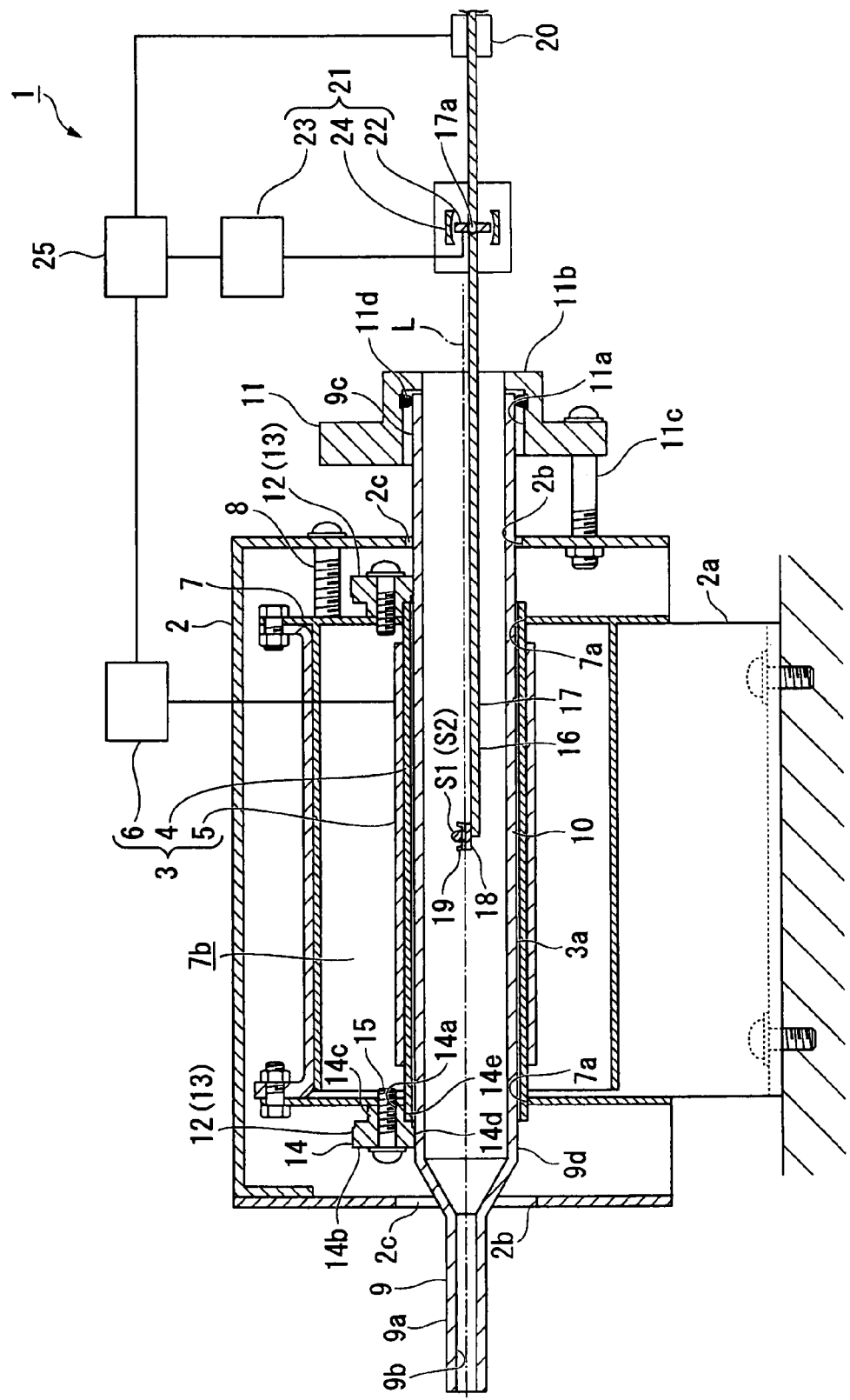
FIG. 1 is a sectional view, as viewed from the side, of a thermal analysis apparatus of an embodiment of this invention.
Figure 2:
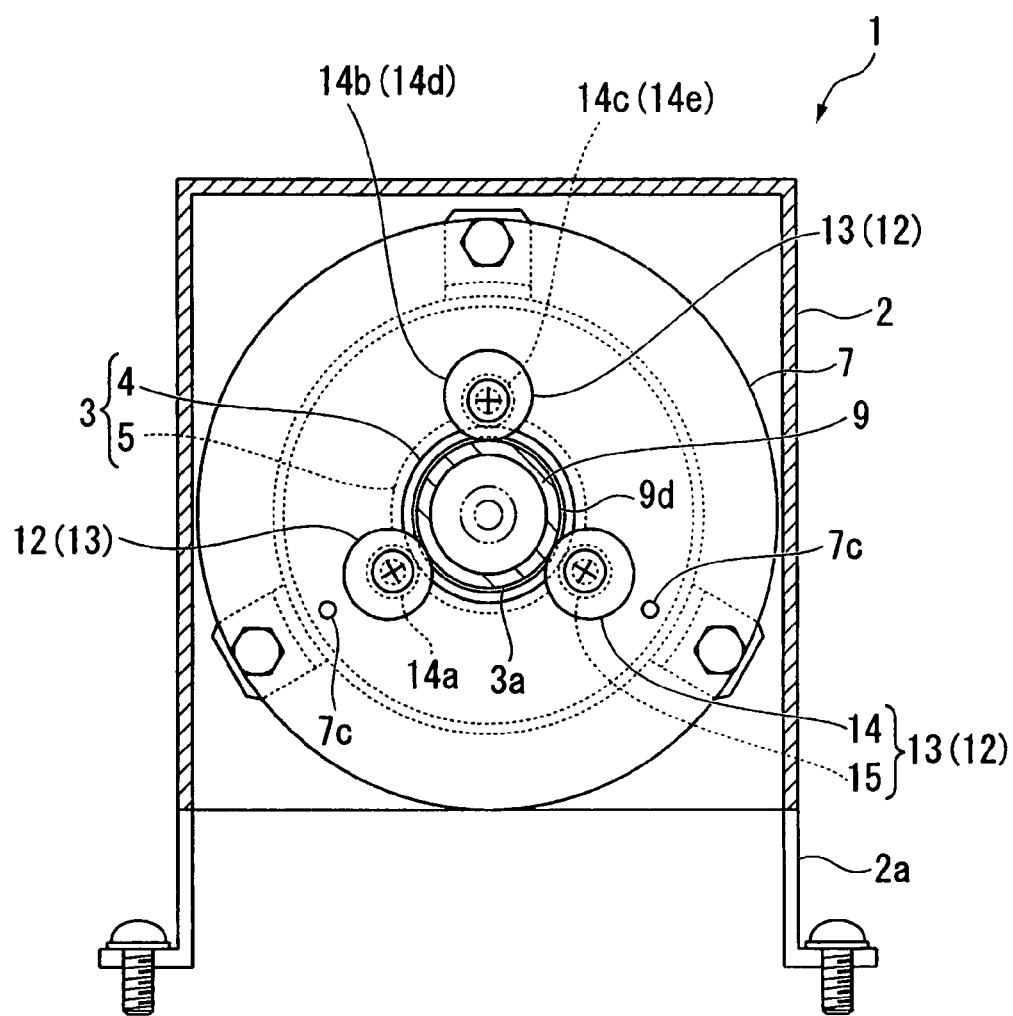
FIG. 2 is a sectional view, as viewed from the front, of the thermal analysis apparatus of the embodiment of this invention.

As shown in FIG. 1 and FIG. 2, the thermal analysis apparatus 1 possesses an outer casing 2 functioning as a support base capable of being fixed to a predetermined installation position, and a heating furnace 3 having been accommodated in an inside of the outer casing 2. The heating furnace 3 possesses an approximately cylindrical furnace core tube 4, a heater 5 which is approximately cylindrical and has been externally fitted to the furnace core tube 4, and a heater drive section 6 having been connected to the heater 5. The heater drive section 6 can raise the heater 5 in its temperature till a predetermined heating temperature and, by raising the heater 5 in its temperature, it is possible to heat an inside of the heating furnace 3 through the furnace core tube 4. Further, the furnace core tube 4 is formed long in comparison with the heater 5, and protrudes from both ends of the heater 5. Further, the outer casing 2 is provided in its lower part with an L-letter like support member 2a, and can be fixed to a floor or the like by the support member 2a. In the inside of the outer casing 2, there is provided a heating furnace fixation part 7 fixing the heating furnace 3 to the outer casing 2, and it is fixed to the outer casing 2 by a support member 8. Incidentally, in FIG. 1, although the support member 8 is shown only in one place, it is deemed that it fixes the heating furnace fixation part 7 in plural places.

The heating furnace fixation part 7 is formed approximately like a hollow circular cylinder and, in its both-side wall parts, through-holes 7a are formed. An inner diameter of the through-hole 7a is set approximately the same as an outer diameter of the furnace core tube 4 of the heating furnace 3 and, by the fact that the through-holes 7a are fitted to both ends of the furnace core tube 4, the heating furnace 3 is fixed to the heating furnace fixation part 7. Further, a closed space 7b is formed by the heating furnace 3 and the heating furnace fixation part 7, the heating furnace fixation part 7 has a temperature keeping action of the heating furnace 3 and, by an adjustment hole 7c shown in FIG. 2, it is also possible to ventilate the closed space 7b, thereby cooling the heating furnace 3 and temperature-adjusting.

Further, in both side wall parts of the outer casing 2, through-holes 2b are formed on the same axis of the through-holes 7a of the heating furnace fixation part 7 having been fixed to the outer casing 2. And, an approximately cylindrical furnace tube 9 is inserted through the heating furnace 3 and the through-holes 2b of the outer casing 2 while having respectively interstices 3a, 2c and, by being inserted through the heating furnace 3, there is formed a heating part 10 that is a range capable of heating in an inside of the heating furnace 3. The furnace tube 9 is formed by alumina for instance, and a reduced diameter exhaust port 9b is formed in a tip part 9a protruding from the outer casing 2. Further, the furnace tube 9 is fixed in its base end part 9c to the outer casing 2 by a fixation member 11. The fixation member 11 possesses an approximately disc-like flange member 11b having been formed with a through-hole 11a to which the furnace tube 9 can be fitted, and a fixation bolt 11c fixing the flange member 11b to the outer casing 2. The furnace tube 9 is fitted and fixed to the through-hole 11a of the flange member 11b through an O-ring 11d.

Further, the furnace tube 9 is positioning-fixed also in both sides of the heating part 10 by two fixation means 12 separately from the fixation member 11. As shown in FIG. 2, each fixation means 12 is constituted by a group of butting members 13, for example, three butting members disposed in three places in a circumferential direction of the furnace tube 9. As shown in FIGS. 1-4, the three butting members of each group lie in a common plane which is perpendicular to the center axis L of the furnace tube 9. The butting member 13 has a columnar piece 14 having a bolt hole 14a, and a fixation bolt 15 which is provided approximately parallel to an axial direction, inserted through the bolt hole 14a, and fixes the columnar piece 14 to a side wall part of the heating furnace fixation part 7. The columnar piece 14 is formed by ceramics, and formed like a step, which is approximately like a column, by a 1st columnar body 14b and a 2nd columnar body 14c, which have large and small different diameters. Further, the bolt hole 14a is formed while penetrating through the 1st columnar body 14b and the 2nd columnar body 14c, and while the 1st columnar body 14b is formed with its center axis being made approximately parallel to and eccentric with respect to a center axis of the bolt hole 14a, the 2nd columnar body 14c is formed such that its center axis becomes the same axis. And, the 1st columnar body 14b of the columnar piece 14 butts in its peripheral face part 14d against an outer periphery face 9d of the furnace tube 9, and the 2nd columnar body 14c butts in its peripheral face part 14e against the furnace core tube 4 of the heating furnace 3. That is, as shown in FIG. 2, while the furnace tube 9 is butting-supported by the three butting members 13 constituting the fixation means 12 and restrained such that there is no positional deviation to a radial direction, it is made possible to slide on the butting member 13 and expand or contract toward an axial direction.

Figure 3:
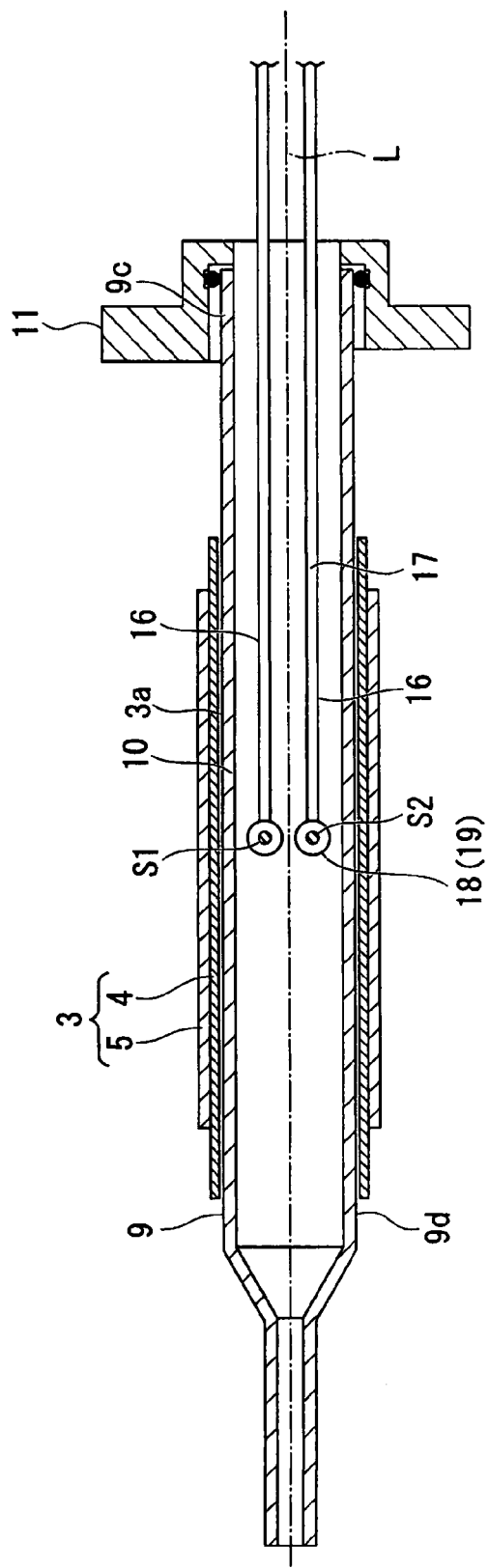
FIG. 3 is an enlarged sectional view, as viewed from above, of a furnace tube in the thermal analysis apparatus of the embodiment of this invention.

Further, as shown in FIG. 1, and FIG. 3, the thermal analysis apparatus 1 possesses two sample holding means 16 holding each of the measurement sample S1 and the reference sample S2 in the inside of the heating part 10 of the furnace tube 9. The sample holding means 16 comprises a balance arm 17 having been rotatably shaft-mounted by a center shaft 17a, and a sample holder 18 having been provided in a tip part of the balance arm 17. As shown in FIG. 3, the two sample holding means 16 are disposed approximately axisymmetrically with respect to a center axis L of the furnace tube 9. The balance arm 17 and the sample holder 18 are formed by platinum for instance. In the sample holder 18, it is possible to dispose a sample container 19 for a sample, which is formed by platinum, and accommodates the measurement sample S1 or the reference sample S2. Further, in the sample holder 18, there is provided a thermocouple not shown in the drawing, that is a temperature measurement means, and it is possible to measure a temperature of the measurement sample S12 or the reference sample S2, which has been disposed in the sample holder 18.

As shown in FIG. 1, in a base end side of the center shaft 17a of the balance arm 17, a position sensor 20 is provided. The position sensor 20 is a photosensor for instance, and can detect whether or not the balance arm 17 is an approximately horizontal state. Additionally, the thermal analysis apparatus 1 possesses, as a weight measurement means 21, a coil 22 having been fixed to the balance arm 17 in a position of the center shaft 17a, a power source 23 for supplying an electric current to the coil 22, and magnets 24 disposed in both sides of the coil 22. That is, by the fact that the electric current is supplied from the power source 23, the coil 22 can adjust a slant of the balance arm 17 by an action with the magnets 24. And, under a control by a control section 25, the electric current is supplied to the coil 22 such that the balance arm 17 is detected to be horizontal by the position sensor 20, and by measuring that electric current it is possible to measure a weight of the sample having been disposed in the sample holder 18 of the balance arm 17. Incidentally, in FIG. 1, although omitted, the position sensor 20 and the weight measurement means 21 are provided in each of the balance arms 17 of the two sample holding means 16, and connected to the control section 25.

Next, there is explained about an action of this thermal analysis apparatus 1. As shown in FIG. 1, first, by the two sample holding means 16, each of the measurement sample S1 and the reference sample S2 is accommodated in the container 19 for sample, thereby disposing it in the sample holder 18. And, first, the control section 25 causes the electric current to be supplied to the coil 22 by the power source 23 in compliance with a detection result of the position sensor 20 such that each of the balance arms 17 becomes approximately horizontal. Next, the control section 25 causes the heater 5 to raise its temperature at a predetermined temperature raising speed by driving the heater drive part 6. And, the inside of the heating part 10 of the furnace tube 9 is heated by the fact that the heating furnace 3 is raised in its temperature, and also the measurement sample S1 and the reference sample S2 are raised in their temperatures. On this occasion, temperature changes of the measurement sample S1 and the reference sample S2 are detected by the thermocouple not shown in the drawing, which is the temperature measurement means having been provided in each of the sample holders 18, and inputted to the control section 25. Further, as to the measurement sample S1 and the reference sample S2, there are seen weight changes resulting from a liquefaction or a gasification at specified temperatures in compliance with respective physical properties. And, following upon the weight changes of the measurement sample S1 and the reference sample S2, although each of the balance arms 17 slants, its result is detected by the position sensor 20 and inputted to the control section 25. On the basis of this detection result of the position sensor 20, the control section 25 causes the electric current to be supplied to the coil 22 by the power source 23 such that the balance arm 17 becomes approximately horizontal. And, by detecting this electric current, it is possible to measure the weight changes of the measurement sample S1 and the reference sample S2, which follow upon the temperature changes. Further, by the fact that, under the control of the control section 25, the balance arm 17 is always kept approximately horizontally, the measurement sample S1 and the reference sample S2 can be disposed so as to always coincide with the center axis L of the furnace tube 9 when seen from a side, so that it is possible to heat while keeping a constant heating environment.

By doing like the above, it is possible to measure the weight change following upon the temperature change of the measurement sample S1, and measure a relative temperature change by comparing with the reference sample S2. Further, by selecting, for the reference sample S2, a matter which has no weight change and is stable in a temperature range to be heated, and measuring a difference in weight between the measurement sample S1 and the reference sample S2, it is possible to countervail a noise other than the weight change of the measurement sample S1 itself, thereby precisely measuring the weight change following upon the temperature change of the measurement sample S1 and evaluating a temperature characteristic of the measurement sample S1.

Here, as mentioned above, following upon raising the heating furnace 3 in its temperature to thereby heat the measurement sample S1 and the reference sample S2, the furnace tube 9 is also heated in the heating part 10, and attempts to expand or contract in the axial direction and the radial direction. The furnace tube 9 is fixed in the base end part 9c by the fixation member 11, and both sides of the heating part 10 are positioning-fixed by the two sets of the fixation means 12 having been constituted by the three butting members 13. That is, while the furnace tube 9 can expand or contract in the axial direction by sliding with respect to the butting member 13, it is certainly positioned and fixed in the radial direction. Therefore, even if the expansion or the contraction has occurred in the axial direction due to the temperature change, while there is no fact that a stress is generated in the furnace tube 9, in the radial direction it is possible to prevent the positional deviation following upon the temperature change.

While a temperature distribution in the inside of the heating part 10 of the furnace tube 9 is uniform in the axial direction, in the radial direction it has the steep temperature distribution toward the center axis L. That is, by making radial positions of the measurement sample S1 and the reference sample S2 in the inside of the furnace tube 9 constant, the heating environments of the measurement sample S1 and the reference sample S2 can be always kept constant. Especially, like the thermal analysis apparatus 1 of the present embodiment, in order to measure the relative change between the measurement sample S1 and the reference sample S2, it is important to keep the heating environments of both constant and, by the fact that it is possible to precisely position in the radial direction by the fixation means 12, it is possible to realize a precise differential thermal analysis. Further, by the fact that the fixation by the fixation means 12 is made the two places in both sides of the heating furnace 10, it is possible to additionally, precisely prevent the positional deviation following upon the temperature change of the furnace tube 9 to the radial direction. Further, both the furnace tube 9 to be heated and the heating furnace 3 heating the furnace tube 9 are fixed to the outer casing 2 through the heating furnace fixation part 7, i.e., fixed by the same fixation system. Therefore, a relative positional relation between the heating furnace 3 and the furnace tube 9 can be kept constant, so that it is possible to additionally stabilize the heating environments of the measurement sample S1 and the reference sample S2.

Further, by the fact that, as to the butting member 13 which butting-supports the furnace tube 9, the columnar piece 14 directly butting against the furnace tube 9 is approximately like the column, a contact with the furnace tube 9 is made a line contact, so that a contact range is made minimum. Therefore, a heat conduction from the furnace tube 9 to the columnar piece 14 of the butting member 13 can be suppressed, so that it is possible to efficiently heat the measurement sample S1 and the reference sample S2, and it is possible to prevent the columnar piece 14 or the fixation bolt 15 from being heated and expanding or contracting. Additionally, by the fact that the columnar piece 14 is formed by ceramics, the heat conduction to the columnar piece 14 can be additionally suppressed, so that it is possible to efficiently heat the measurement sample S1 and the reference sample S2, and it is possible to suppress the expansion or the contraction of the columnar piece 14 due to the fact that it is heated.

Figure 4:
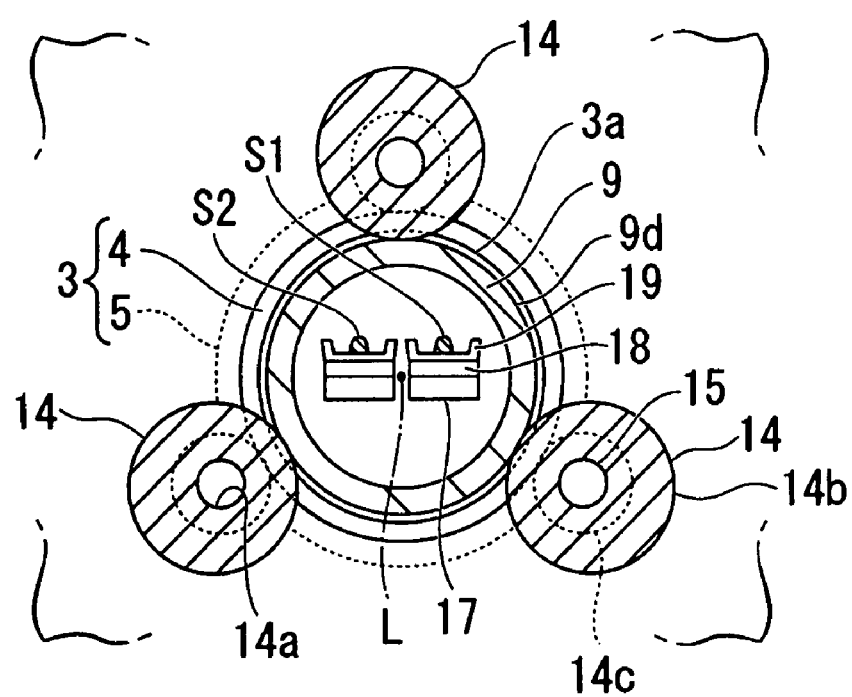
FIG. 4 is an enlarged sectional view, as viewed from the front, of the furnace tube in the thermal analysis apparatus of the embodiment of this invention.

Further, as shown in FIG. 4, as to the columnar piece 14 of the butting member 13, while the 2nd columnar body 14c butting against the furnace core tube 4 of the heating furnace 3 is fixed such that its center axis becomes the same axis with respect to the fixation bolt 15 having been provided approximately parallel to the axial direction, the 1st columnar body 14b butting against the furnace tube 9 is fixed with its center axis being made eccentric. That is, by changing a direction in which the columnar piece 14 is fixed with the fixation bolt 15 being made a center, it is possible to adjust a radial position of the furnace tube 9 butted against and fixed to the columnar piece 14. By this mechanism, the measurement sample S1 and the reference sample S2 can be adjusted to a middle position in which a temperature gradient of the furnace tube 9 becomes minimal, i.e., becomes approximately symmetric in the center axis L.

Like the above, in the thermal analysis apparatus 1 of this embodiment, by positioning-fixing the furnace tube 9, which has been fixed in the base end part 9c by the fixation member 11, additionally by the fixation means 12, there is no fact that the furnace tube 9 deviates in its position in the radial direction due to the temperature change, so that it is possible to perform the thermal analysis by heating the measurement sample S1 and the reference sample S2 always in a constant heating environment.

Incidentally, in the thermal analysis apparatus 1 of the present embodiment, although there has been made one in which there are possessed the two sample holding means 16 holding the samples in the inside of the furnace tube 9, and the thermal analyses of the measurement sample S1 and the reference sample S2 are performed, there is not limited to this. Also in a case where only the weight change following upon the temperature change of the measurement sample 1 is measured while having at least one sample holding means 16, it is possible to heat the measurement sample S1 in the constant heating environment, and it is possible to perform a precise thermogravimetric analysis. Further, in the present embodiment, although the furnace tube 9 is made one disposed approximately horizontally, there may made one in which the similar measurement is performed, e.g., by disposing the sample in the inside by the sample holding means from above or below the furnace tube having been disposed vertically. Additionally, as mentioned above, it is not one limited to the differential thermal/thermogravimetric analysis, and can be applied to various thermal analyses.

Further, although the fixation means 12 has been made one constituted by the three butting members 13, it is not limited to this and, if it is possible to fix the furnace tube 9 in at least three or more places in a circumferential direction, it is possible to expect the similar effects. Further, although the fixation means 12 has been made one provided in the two places in both sides of the heating part 10, it is not one limited to this and, if it is provided in at least one place in the axial direction, it is possible to make the furnace tube 9 capable of expanding or contracting in the axial direction, and positioning-fix it in the radial direction.

In the above, about the embodiment of the present invention, although there has been detailedly mentioned by referring to the drawings, a concrete constitution is not one limited to this embodiment, and there are included also a design change in a scope not deviating from a gist of the present invention, and the like.

What is claimed is:

1. A thermal analysis apparatus comprising:
   a support base;
   a heating furnace having an approximately cylinder shape and whose inside can be raised in temperature;
   a heating furnace fixation part which fixes the heating furnace to the support base;
   a furnace tube which has an approximately cylinder shape, which is inserted through the heating furnace with an interstice therebetween, and which is fixed at a base end part thereof to the support base by a fixation member;
   fixation means for fixing the position of the furnace tube in a radial direction and permitting expansion and contraction of the furnace tube in an axial direction, the fixation means comprising at least three butting members which butt against the furnace tube in at least three places in a circumferential direction;
   sample holding means for holding a sample inside a heating part of the furnace tube that is heated by the heating furnace; and
   temperature measurement means for measuring a temperature change of the sample.

2. A thermal analysis apparatus according to claim 1; wherein the fixation means is provided at a tip side and at a base end side of the heating part of the furnace tube.

3. A thermal analysis apparatus according to claim 1; wherein the fixation means is provided in the heating furnace fixation part, and the furnace tube is fixed to the support base by the fixation means through the heating furnace fixation part.

4. A thermal analysis according to claim 1; further including weight measurement means for measuring a weight of the sample held by the sample holding means.

5. A thermal analysis apparatus according to claim 1; including two sample holding means and corresponding temperature measurement means disposed in approximately axisymmetric relation with respect to a center axis of the furnace tube.

6. A thermal analysis apparatus according to claim 1; wherein each butting member of the fixation means is fixed with respect to the support base by a fixation bolt and has a columnar piece whose peripheral face butts against the furnace tube.

7. A thermal analysis apparatus according to claim 6; wherein the columnar piece is formed of ceramic.

8. A thermal analysis apparatus according to claim 6; wherein the columnar piece of each butting member is eccentric with respect to the fixation bolt.

9. A thermal analysis apparatus comprising:
   a heating furnace; a furnace tube extending in an axial direction in the heating furnace; at least one sample holder extending axially inside the furnace tube; and three or more butting members disposed in circumferentially spaced-apart relationship about the furnace tube on the outside thereof and butting against the furnace tube to restrain positional deviation thereof in a radial direction during heating of the furnace tube by the heating furnace.

10. A thermal analysis apparatus according to claim 9; further including weight measurement means for measuring the weight of a sample held by the sample holder.

11. A thermal analysis apparatus according to claim 9; wherein the butting members are configured to permit expansion and contraction of the furnace tube in the axial direction.

12. A thermal analysis apparatus according to claim 9; wherein the butting members lie in a common plane.

13. A thermal analysis apparatus according to claim 9; comprising at least two groups of the three or more butting members, the groups of butting members being axially spaced from one another along the furnace tube.

14. A thermal analysis apparatus according to claim 13; wherein the butting members of each group lie in a common plane.

15. A thermal analysis apparatus according to claim 9; wherein each butting member has a peripheral face that butts against the furnace tube and is eccentrically mounted to enable adjustment of the radial position of the furnace tube.

16. A thermal analysis apparatus according to claim 15; wherein the peripheral face is composed of ceramic.

17. A thermal analysis apparatus according to claim 9; wherein each butting member is fixed with respect to the heating furnace by a bolt and has a peripheral face that butts against the furnace tube and that is eccentric with respect to the bolt.

18. A thermal analysis apparatus according to claim 17; wherein the peripheral face is composed of ceramic.

19. A thermal analysis apparatus according to claim 9; further including temperature measurement means for measuring a temperature change of a sample held by the sample holder.

20. A thermal analysis apparatus according to claim 19; further including weight measurement means for measuring the weight of a sample held by the sample holder.

* * * * *